(12) United States Patent
Hoffman et al.

(10) Patent No.: US 10,051,893 B2
(45) Date of Patent: Aug. 21, 2018

(54) APPARATUS AND METHOD FOR COMMUNICATION AND NEGOTIATION OF CHARGE RATE BETWEEN ELECTRONIC SMOKING DEVICE AND CHARGER

(71) Applicant: Fontem Holdings 1 B.V., Amsterdam (NL)

(72) Inventors: Adam Hoffman, Campbell, CA (US); James R. Conrey, San Jose, CA (US)

(73) Assignee: Fontem Holdings 1 B.V., Amsterdam (NL)

( * ) Notice: Subject to any disclaimer, the term of this patent is extended or adjusted under 35 U.S.C. 154(b) by 0 days.

(21) Appl. No.: 15/219,195

(22) Filed: Jul. 25, 2016

(65) Prior Publication Data

US 2018/0020727 A1 Jan. 25, 2018

(51) Int. Cl.
| | | |
|---|---|---|
| *A24F 47/00* | (2006.01) | |
| *H05B 1/02* | (2006.01) | |
| *H05B 3/03* | (2006.01) | |
| *G06F 1/32* | (2006.01) | |
| *H02J 7/00* | (2006.01) | |
| *A61M 15/06* | (2006.01) | |
| *A61M 11/04* | (2006.01) | |

(52) U.S. Cl.
CPC ......... *A24F 47/008* (2013.01); *A61M 11/042* (2014.02); *A61M 15/06* (2013.01); *G06F 1/3296* (2013.01); *H02J 7/0042* (2013.01); *H02J 7/0052* (2013.01); *H05B 1/0297* (2013.01); *H05B 3/03* (2013.01); *A61M 2205/35* (2013.01)

(58) Field of Classification Search
CPC ...... A24F 47/008; A24F 47/002; A24F 47/00; Y02E 60/12; H02J 7/0044; H02J 7/0042
USPC .................................................. 320/114, 115
See application file for complete search history.

(56) References Cited

U.S. PATENT DOCUMENTS

| | | | |
|---|---|---|---|
| 8,851,081 B2 | 10/2014 | Fernando | |
| 9,497,999 B2 * | 11/2016 | Lord | A24F 47/008 |
| 9,572,372 B2 * | 2/2017 | Liu | A24F 47/008 |

(Continued)

FOREIGN PATENT DOCUMENTS

| | | |
|---|---|---|
| EP | 2959786 A1 | 12/2015 |
| WO | 2014008646 A1 | 1/2014 |

(Continued)

*Primary Examiner* — Gary Paumen
(74) *Attorney, Agent, or Firm* — Dykema Gossett PLLC (57) ABSTRACT

Aspects of the instant disclosure relate to electronic cigarettes; more particularly, to electronic cigarettes and chargers. In various embodiments, the e-cigarette includes a power supply portion comprising a power supply, an atomizer/liquid reservoir portion comprising a liquid reservoir and an atomizer, the atomizer operable when connected to the power supply to atomize liquid stored in the liquid reservoir, and control electronics, where the control electronics are configured to execute a set of computer readable instructions to place the electronic smoking device in an operation mode, a communication mode, and a charge mode. Aspects of the disclosure are directed to a charger for an electronic smoking device. Aspects of the disclosure are further directed to a system comprising an electronic smoking device and a charger. Aspects of the disclosure are further directed to a method for charging an electronic smoking device.

20 Claims, 5 Drawing Sheets

(56) References Cited

U.S. PATENT DOCUMENTS

| | | | |
|---|---|---|---|
| 9,635,886 B2* | 5/2017 | Tu | A24F 47/008 |
| 9,675,114 B2* | 6/2017 | Timmermans | A24F 47/008 |
| 2011/0265806 A1 | 11/2011 | Alarcon et al. | |
| 2013/0284192 A1 | 10/2013 | Peleg et al. | |
| 2013/0340775 A1 | 12/2013 | Juster et al. | |
| 2014/0014125 A1* | 1/2014 | Fernando | A24F 47/008 131/328 |
| 2014/0053856 A1* | 2/2014 | Liu | A24F 47/008 131/329 |
| 2014/0107815 A1 | 4/2014 | LaMothe | |
| 2014/0123989 A1 | 5/2014 | LaMothe | |
| 2014/0123990 A1* | 5/2014 | Timmermans | A24F 47/008 131/328 |
| 2014/0174459 A1 | 6/2014 | Burstyn | |
| 2014/0278250 A1 | 9/2014 | Smith et al. | |
| 2014/0278258 A1 | 9/2014 | Shafer | |
| 2014/0305820 A1* | 10/2014 | Xiang | A24F 15/18 206/236 |
| 2014/0345633 A1 | 11/2014 | Talon et al. | |
| 2015/0002076 A1* | 1/2015 | Xiang | H02J 7/045 320/107 |
| 2015/0036250 A1* | 2/2015 | Xiang | H02J 7/0029 361/78 |
| 2015/0100441 A1* | 4/2015 | Alarcon | G06Q 20/18 705/16 |
| 2015/0114408 A1* | 4/2015 | Lord | A24F 47/008 131/329 |
| 2015/0128975 A1* | 5/2015 | Alarcon | A24F 47/008 131/329 |
| 2015/0136153 A1* | 5/2015 | Lord | A24F 47/008 131/328 |
| 2015/0173419 A1* | 6/2015 | Tu | A24F 47/008 131/329 |
| 2015/0189916 A1* | 7/2015 | Wu | A24F 47/008 219/510 |
| 2015/0189917 A1* | 7/2015 | Xiang | H01M 10/44 131/328 |
| 2015/0224268 A1 | 8/2015 | Henry et al. | |
| 2015/0237918 A1* | 8/2015 | Liu | A24F 47/008 131/328 |
| 2015/0245660 A1* | 9/2015 | Lord | H04W 8/24 131/328 |
| 2015/0257448 A1* | 9/2015 | Lord | A24F 47/008 700/90 |
| 2015/0258289 A1 | 9/2015 | Henry, Jr. et al. | |
| 2015/0272223 A1* | 10/2015 | Weigensberg | G01R 31/3606 131/328 |
| 2015/0313284 A1* | 11/2015 | Liu | H05B 1/0244 131/329 |
| 2015/0327596 A1* | 11/2015 | Alarcon | A24F 47/008 131/328 |
| 2015/0332379 A1* | 11/2015 | Alarcon | A24F 15/18 705/26.81 |
| 2015/0333542 A1* | 11/2015 | Alarcon | H02J 7/007 131/328 |
| 2015/0357839 A1* | 12/2015 | Cai | A24F 47/008 131/329 |
| 2016/0057811 A1* | 2/2016 | Alarcon | H05B 1/0252 219/494 |
| 2016/0106156 A1* | 4/2016 | Qiu | A24F 47/008 392/404 |
| 2016/0143359 A1* | 5/2016 | Xiang | H05B 1/0227 392/387 |
| 2016/0206000 A1* | 7/2016 | Lord | A24F 47/008 |
| 2016/0226286 A1* | 8/2016 | Xiang | A24F 47/002 |
| 2016/0227840 A1* | 8/2016 | Xiang | A24F 47/008 |
| 2016/0227842 A1* | 8/2016 | Xiang | A24F 47/008 |
| 2016/0242466 A1* | 8/2016 | Lord | G06F 1/3296 |
| 2016/0285983 A1* | 9/2016 | Liu | A24F 47/002 |
| 2016/0342767 A1* | 11/2016 | Narasimhan | G06F 19/3456 |
| 2016/0345627 A1* | 12/2016 | Liu | A24F 47/008 |
| 2016/0360788 A1* | 12/2016 | Wang | A24F 47/008 |
| 2017/0000192 A1* | 1/2017 | Li | A24F 47/008 |
| 2017/0042215 A1* | 2/2017 | Murison | A24F 15/12 |
| 2017/0049151 A1* | 2/2017 | Xue | H05B 1/0244 |
| 2017/0079329 A1* | 3/2017 | Zitzke | A24F 47/008 |
| 2017/0118584 A1* | 4/2017 | Xiang | A24F 47/008 |
| 2017/0360103 A1* | 12/2017 | Li | A24F 47/008 |

FOREIGN PATENT DOCUMENTS

| | | |
|---|---|---|
| WO | 2014029880 A2 | 2/2014 |
| WO | 2015023996 A2 | 2/2015 |
| WO | 2015158482 A1 | 10/2015 |
| WO | 2016023809 A1 | 2/2016 |

* cited by examiner

APPARATUS AND METHOD FOR COMMUNICATION AND NEGOTIATION OF CHARGE RATE BETWEEN ELECTRONIC SMOKING DEVICE AND CHARGER

BACKGROUND a. Field

The present invention relates generally to electronic smoking devices and in particular electronic cigarettes.

b. Background Art

An electronic smoking device, such as an electronic cigarette (or e-cigarette or eCig), typically has a housing accommodating an electric power source (e.g., a single use or rechargeable battery, electrical plug, or other power source), and an electrically operable atomizer. The atomizer vaporizes or atomizes liquid supplied from a reservoir and provides vaporized or atomized liquid as an aerosol. Control electronics control the activation of the atomizer. In some electronic cigarettes, an airflow sensor is provided within the electronic smoking device, which detects a user puffing on the device (e.g., by sensing an under-pressure or an airflow pattern through the device). The airflow sensor indicates or signals the puff to the control electronics to power up the device and generate vapor. In other e-cigarettes, a switch is used to power up the e-cigarette to generate a puff of vapor.

BRIEF SUMMARY

In accordance with one aspect of the present invention there is provided an electronic smoking device comprising a power supply portion comprising a power supply, an atomizer/liquid reservoir portion comprising a liquid reservoir and an atomizer, the atomizer operable when connected to the power supply to atomize liquid stored in the liquid reservoir, and control electronics, wherein the control electronics are configured to execute a set of computer-readable instructions to place the electronic smoking device in an operation mode, a communication mode, and a charge mode.

In accordance with another aspect of the present invention there is provided a charger for an electronic smoking device comprising a first connection, wherein the first connection further comprises a plurality of connecting pins for electrically connecting to the electronic smoking device, a second connection, wherein the second connection is configured for electrically connecting to a computing device, charger control electronics, wherein the charger control electronics comprises a memory, wherein the memory further comprises a set of computer-readable instructions to place the charger in an idle mode, a communication mode and a charge mode.

In accordance with another aspect of the present invention there is provided a system comprising an electronic smoking device comprising a battery, an eCig memory storing a first set of computer-readable instructions, and control electronics configured to execute the first set of computer-readable instructions to place the electronic smoking device in a first plurality of modes; and a charger comprising a charger memory storing a second set of computer-readable instructions, and a charger processor configured to execute the second set of computer-readable instructions to place the charger in a second plurality of modes; wherein each of the first plurality of modes has at least one complementary mode in the second plurality of modes, and wherein the control electronics and the charger processor are configured to communicate and to negotiate a charge rate for charging the battery when the electronic smoking device is electrically connected to the charger.

In accordance with yet another aspect of the present invention there is provided a method for charging an electronic smoking device comprising connecting the electronic smoking device to a charger, wherein control electronics of the electronic smoking device are in a first eCig mode and wherein a charger processor of the charger is in a first charger mode, switching the control electronics from the first eCig mode to a second eCig mode, switching the charger processor from the first charger mode to a second charger mode, negotiating, between the control electronics and the charger processor, while the electronic smoking device is in the second eCig mode, and while a charge rate for charging a battery of the electronic smoking device, the charger is in the second charger mode, and charging the battery at the negotiated charge rate.

The characteristics, features and advantages of these embodiments and the manner in which they are obtained as described above, will become more apparent and be more clearly understood in connection with the following description of exemplary embodiments, which are explained with reference to the accompanying drawings.

BRIEF DESCRIPTION OF THE DRAWINGS

In the drawings, the same element numbers indicate the same elements in each of the views.

DETAILED DESCRIPTION OF EMBODIMENTS

Figure 1:
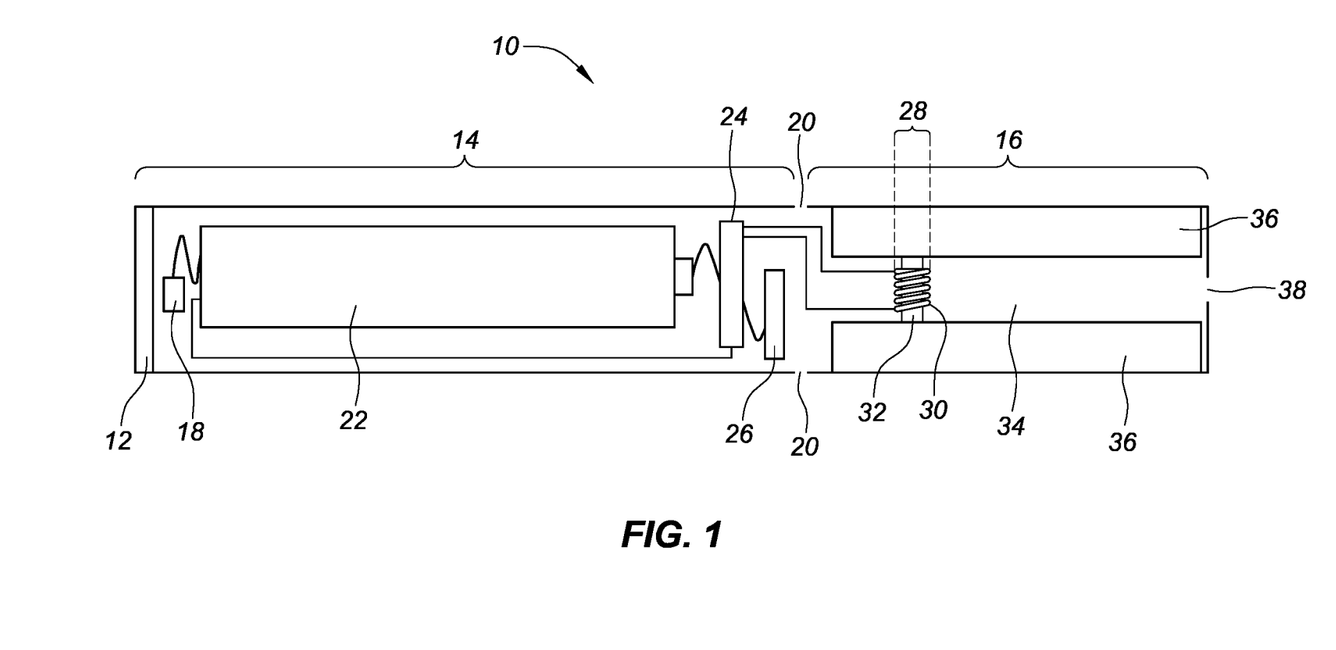
FIG. 1 is a schematic cross-sectional illustration of an exemplary e-cigarette.

Throughout the following, an electronic smoking device will be exemplarily described with reference to an e-cigarette. As is shown in FIG. 1, an e-cigarette 10 typically has a housing comprising a cylindrical hollow tube having an end cap 12. The cylindrical hollow tube may be a single-piece or a multiple-piece tube. In FIG. 1, the cylindrical hollow tube is shown as a two-piece structure having a power supply portion 14 and an atomizer/liquid reservoir portion 16. Together the power supply portion 14 and the atomizer/liquid reservoir portion 16 form a cylindrical tube which can be approximately the same size and shape as a conventional cigarette, typically about 100 mm with a 7.5 mm diameter, although lengths may range from 70 to 150 or 180 mm, and diameters from 5 to 28 mm.

The power supply portion 14 and atomizer/liquid reservoir portion 16 are typically made of metal (e.g., steel or aluminum, or of hardwearing plastic) and act together with the end cap 12 to provide a housing to contain the components of the e-cigarette 10. The power supply portion 14 and the atomizer/liquid reservoir portion 16 may be configured to fit together by, for example, a friction push fit, a snap fit, a bayonet attachment, a magnetic fit, or screw threads. The end cap 12 is provided at the front end of the power supply portion 14. The end cap 12 may be made from translucent plastic or other translucent material to allow a light-emitting diode (LED) 18 positioned near the end cap to emit light through the end cap. Alternatively, the end cap may be made of metal or other materials that do not allow light to pass.

An air inlet may be provided in the end cap, at the edge of the inlet next to the cylindrical hollow tube, anywhere along the length of the cylindrical hollow tube, or at the connection of the power supply portion 14 and the atomizer/liquid reservoir portion 16. FIG. 1 shows a pair of air inlets 20 provided at the intersection between the power supply portion 14 and the atomizer/liquid reservoir portion 16.

A power supply, preferably a battery 22, the LED 18, control electronics 24 and, optionally, an airflow sensor 26 are provided within the cylindrical hollow tube power supply portion 14. The battery 22 is electrically connected to the control electronics 24, which are electrically connected to the LED 18 and the airflow sensor 26. In this example, the LED 18 is at the front end of the power supply portion 14, adjacent to the end cap 12; and the control electronics 24 and airflow sensor 26 are provided in the central cavity at the other end of the battery 22 adjacent the atomizer/liquid reservoir portion 16.

The airflow sensor 26 acts as a puff detector, detecting a user puffing or sucking on the atomizer/liquid reservoir portion 16 of the e-cigarette 10. The airflow sensor 26 can be any suitable sensor for detecting changes in airflow or air pressure, such as a microphone switch including a deformable membrane which is caused to move by variations in air pressure. Alternatively, the sensor may be, for example, a Hall element or an electro-mechanical sensor.

The control electronics 24 are also connected to an atomizer 28. In the example shown, the atomizer 28 includes a heating coil 30 which is wrapped around a wick 32 extending across a central passage 34 of the atomizer/liquid reservoir portion 16. The central passage 34 may, for example, be defined by one or more walls of the liquid reservoir and/or one or more walls of the atomizer/liquid reservoir portion 16 of the e-cigarette 10. The coil 30 may be positioned anywhere in the atomizer 28 and may be transverse or parallel to a longitudinal axis of a cylindrical liquid reservoir 36. The wick 32 and heating coil 30 do not completely block the central passage 34. Rather an air gap is provided on either side of the heating coil 30 enabling air to flow past the heating coil 30 and the wick 32. The atomizer may alternatively use other forms of heating elements, such as ceramic heaters, or fiber or mesh material heaters. Nonresistance heating elements such as sonic, piezo, and jet spray may also be used in the atomizer in place of the heating coil.

The central passage 34 is surrounded by the cylindrical liquid reservoir 36 with the ends of the wick 32 abutting or extending into the liquid reservoir 36. The wick 32 may be a porous material such as a bundle of fiberglass fibers or cotton or bamboo yarn, with liquid in the liquid reservoir 36 drawn by capillary action from the ends of the wick 32 towards the central portion of the wick 32 encircled by the heating coil 30.

The liquid reservoir 36 may alternatively include wadding (not shown in FIG. 1) soaked in liquid which encircles the central passage 34 with the ends of the wick 32 abutting the wadding. In other embodiments, the liquid reservoir may comprise a toroidal cavity arranged to be filled with liquid and with the ends of the wick 32 extending into the toroidal cavity.

An air inhalation port 38 is provided at the back end of the atomizer/liquid reservoir portion 16 remote from the end cap 12. The inhalation port 38 may be formed from the cylindrical hollow tube atomizer/liquid reservoir portion 16 or may be formed in an end cap.

In use, a user sucks on the e-cigarette 10. This causes air to be drawn into the e-cigarette 10 via one or more air inlets, such as air inlets 20, and to be drawn through the central passage 34 towards the air inhalation port 38. The change in air pressure which arises is detected by the airflow sensor 26, which generates an electrical signal that is passed to the control electronics 24. In response to the signal, the control electronics 24 activate the heating coil 30, which causes liquid present in the wick 32 to be vaporized creating an aerosol (which may comprise gaseous and liquid components) within the central passage 34. As the user continues to suck on the e-cigarette 10, this aerosol is drawn through the central passage 34 and inhaled by the user. At the same time, the control electronics 24 also activate the LED 18 causing the LED 18 to light up, which is visible via the translucent end cap 12. Activation of the LED may mimic the appearance of a glowing ember at the end of a conventional cigarette. As liquid present in the wick 32 is converted into an aerosol, more liquid is drawn into the wick 32 from the liquid reservoir 36 by capillary action and thus is available to be converted into an aerosol through subsequent activation of the heating coil 30.

Some e-cigarette are intended to be disposable and the electric power in the battery 22 is intended to be sufficient to vaporize the liquid contained within the liquid reservoir 36, after which the e-cigarette 10 is thrown away. In other embodiments, the battery 22 is rechargeable and the liquid reservoir 36 is refillable. In the cases where the liquid reservoir 36 is a toroidal cavity, this may be achieved by refilling the liquid reservoir 36 via a refill port (not shown in FIG. 1). In other embodiments, the atomizer/liquid reservoir portion 16 of the e-cigarette 10 is detachable from the power supply portion 14 and a new atomizer/liquid reservoir portion 16 can be fitted with a new liquid reservoir 36 thereby replenishing the supply of liquid. In some cases, replacing the liquid reservoir 36 may involve replacement of the heating coil 30 and the wick 32 along with the replacement of the liquid reservoir 36. A replaceable unit comprising the atomizer 28 and the liquid reservoir 36 may be referred to as a cartomizer.

The new liquid reservoir may be in the form of a cartridge (not shown in FIG. 1) defining a passage (or multiple passages) through which a user inhales aerosol. In other embodiments, the aerosol may flow around the exterior of the cartridge to the air inhalation port 38.

Of course, in addition to the above description of the structure and function of a typical e-cigarette 10, variations also exist. For example, the LED 18 may be omitted. The airflow sensor 26 may be placed, for example, adjacent to the end cap 12 rather than in the middle of the e-cigarette. The airflow sensor 26 may be replaced by, or supplemented with, a switch which enables a user to activate the e-cigarette manually rather than in response to the detection of a change in airflow or air pressure.

Different types of atomizers may be used. Thus, for example, the atomizer may have a heating coil in a cavity in the interior of a porous body soaked in liquid. In this design, aerosol is generated by evaporating the liquid within the porous body either by activation of the coil heating the porous body or alternatively by the heated air passing over or through the porous body. Alternatively the atomizer may use a piezoelectric atomizer to create an aerosol either in combination or in the absence of a heater.

Figure 2:
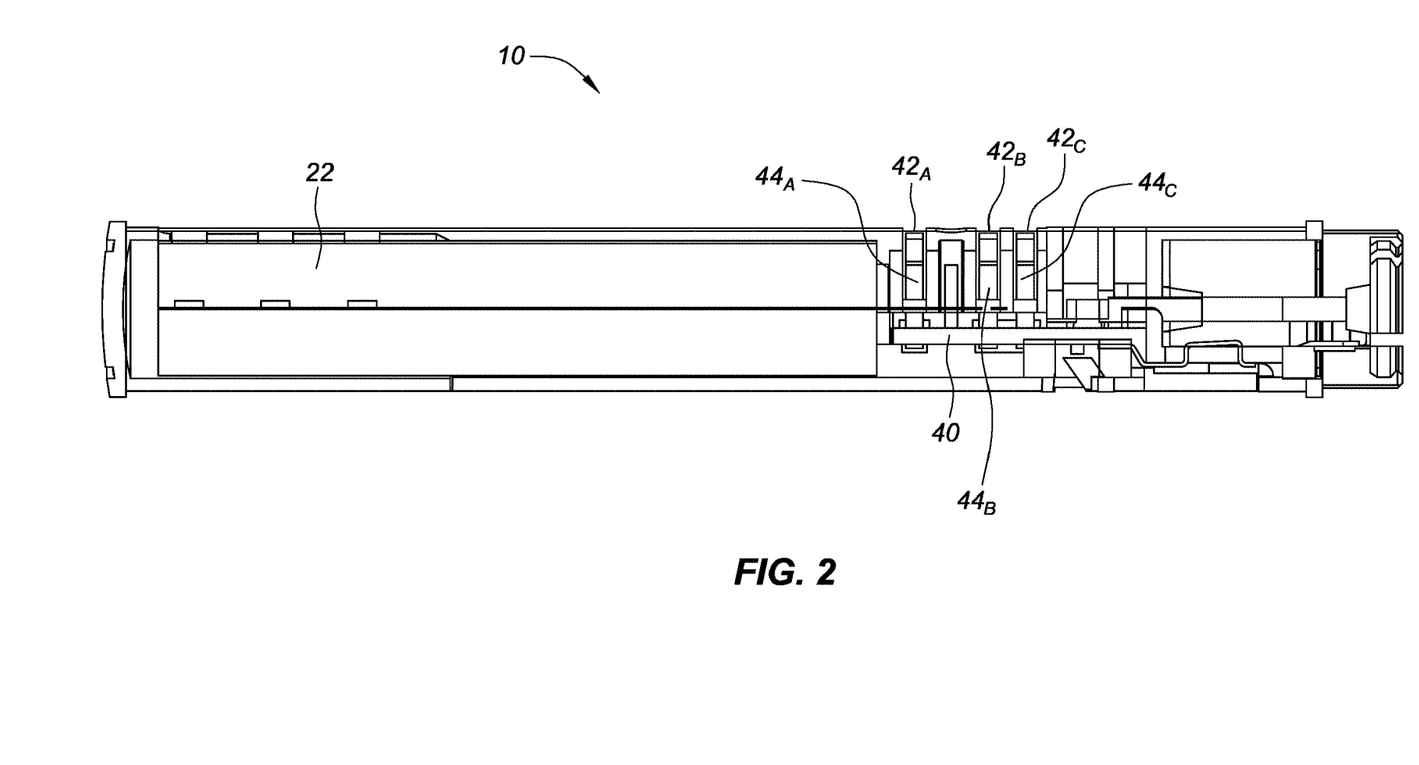
FIG. 2 is a cross-sectional side view of an e-cigarette, consistent with various aspects of the present disclosure.

FIG. 2 is a cross-sectional side view of an e-cigarette, consistent with various aspects of the present disclosure. As shown in FIG. 2, the e-cigarette 10 can include a battery 22 and a controller circuitry 40. Electrical contact apertures $42_{A-C}$ can be located on the e-cigarette 10. Electrical contacts or connectors $44_{A-C}$ can be electrically coupled with the controller circuitry 40, and extend through at least a portion of the electrical contact apertures $42_{A-C}$. As discussed in more detail below, the electrical connectors $44_{A-C}$ facilitate electrical communication between the controller circuitry 40 and external circuitry, as well as charging of the battery 22 by transmitting a current to the battery 22 from an external power source (e.g., external battery, charger, electronic device, among others).

The e-cigarette 10 can utilize software, hardware, firmware, and/or logic to perform a number of functions described herein. The e-cigarette 10 can include a combination of hardware and instructions to share information. The hardware, for example can include the controller circuitry 40 and/or a memory (not shown) (e.g., non-transitory computer-readable medium (CRM) database, etc.). The memory, as used herein, can include a number of processors capable of executing instructions stored by the memory resource. The memory can be integrated in a single device or distributed across multiple devices. The instructions (e.g., computer-readable instructions) can include instructions stored on the memory and executable by the memory for providing control over the e-cigarette 10 and/or performing various steps discussed in relation to FIGS. 4 and 5, in an example.

Figure 3A:
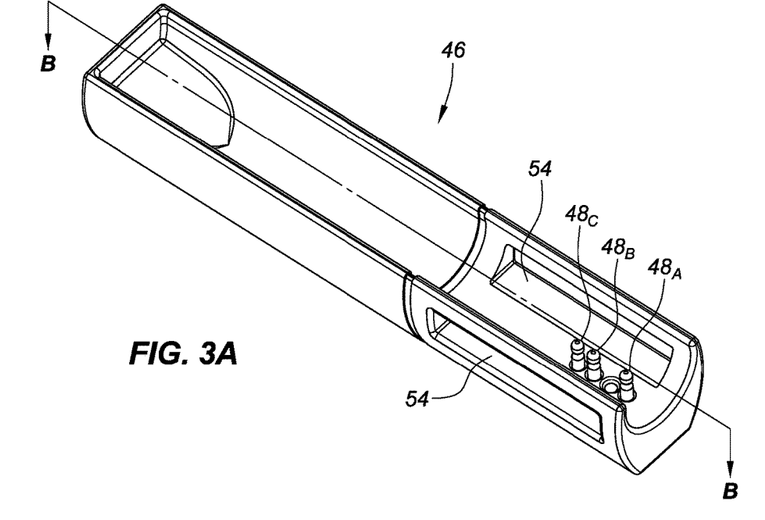
FIG. 3A is an isometric side and top view of a charger for the e-cigarette shown in FIG. 2, consistent with various aspects of the present disclosure.
Figure 3B:
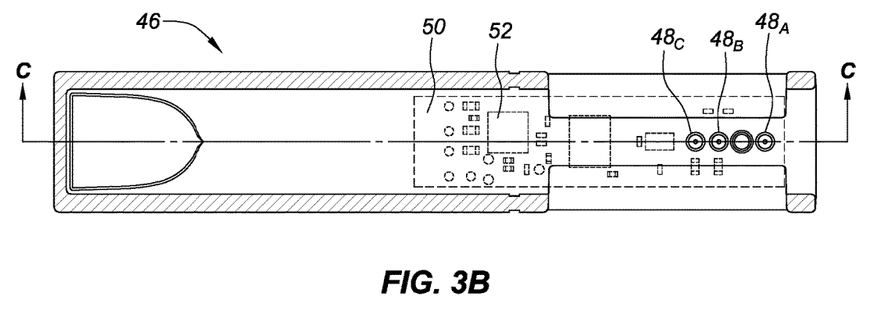
FIG. 3B is a top, cross-sectional view of the charger shown in FIG. 3A, taken along line B-B of FIG. 3A, consistent with various aspects of the present disclosure.
Figure 3C:
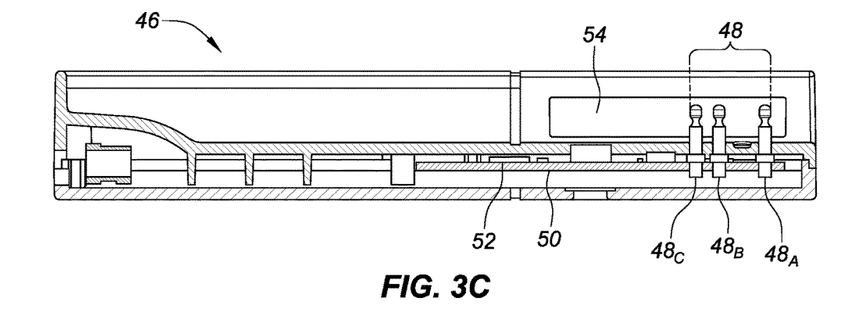
FIG. 3C is a side, cross-sectional view of the charger shown in FIGS. 3A and 3B, taken along line C-C of FIG. 3B, consistent with various aspects of the present disclosure.

FIGS. 3A-C are a drawings that shows an exemplary embodiment of the charger for charging a battery of the e-cigarette. FIG. 3A is an isometric side and top view of a charger for the e-cigarette shown in FIG. 2, consistent with various aspects of the present disclosure. FIG. 3B is a top, cross-sectional view of the charger shown in FIG. 3A, taken along line B-B of FIG. 3A, consistent with various aspects of the present disclosure. FIG. 3C is a side, cross-sectional view of the charger shown in FIGS. 3A and 3B, taken along line C-C of FIG. 3B, consistent with various aspects of the present disclosure.

A plurality of connecting pins $48_{A-C}$ can be configured to electrically connect to a plurality of connectors $44_{A-C}$ in the e-cigarette 10. As shown in an exemplary embodiment in FIGS. 3A-C, the charger 46 can have three connecting pins $48_{A-C}$. The number of connectors $44_{A-C}$/connecting pins $48_{A-C}$ can range from, for example, 2-20. The connecting pins $48_{A-C}$ can have, for example a round cross-section and be cylindrically shaped. Other embodiments can use different sizes or shapes for the connecting pins (e.g., one round, one square, smaller or larger diameter and/or length, etc.) to aid with the desired configuration of the connection between the e-cigarette 10 and the charger 46.

The three connecting pins $48_{A-C}$ can be used to connect with the corresponding connectors $44_{A-C}$ in the e-cigarette 10 for charging the battery 22 and to facilitate signals or messages between the e-cigarette 10 and the charger 46. For example, a connecting pin $48_C$ can be connected to a ground and a connecting pin $48_B$ can be used for transmitting current from to a charging circuit, and a connecting pin $48_A$ can be used for sending a transmission of one or more signals or messages from the charger 46 to the e-cigarette 10 (e.g., sending a charge message, or a disconnect message, etc.). The connecting pin $48_B$ can, in some embodiments, be used to by the e-cigarette 10 to receive a signal or transmission from the charger 46 when the e-cigarette 10 is in the communication mode (and not in the charging mode). The signal going through the connector $48_B$ can be, for example, a high or a low signal. In some embodiments, the high and/or low signals can be used to trigger a switch between modes described in greater detail below.

In other embodiments, the arrangement/order of the connectors/connecting pins can be varied (e.g., connector/connecting pin $44_A/48_A$ is ground, connector/connecting pin $44_B/48_B$ is hot, connector/connecting pin $44_C/48_C$ is sending/receiving, or connector $44_A/48_A$ is hot, connector/connecting pin $44_B/48_B$ is ground, and connector/connecting pin $44_C/48_C$ is for sending/receiving, etc.). Additional connectors/connecting pins could be used (e.g., four connectors/connecting pins) to permit dedicated paths for sending and receiving signals. However, due to space constraints, a single connector that alternates between acting as the path that can send and receive signals can reduce the size of space needed in the e-cigarette 10 for the connectors.

The connectors/connecting pins can also be arranged in a configuration to prevent reversing a connection between the e-cigarette 10 and the charger 46. For example, the spacing of the connectors/connecting pins can vary so that the charger 46 only connects to the e-cigarette 10 in one configuration. For example, a distance between connectors $44_A$ and $44_B$ can be different from the distance between connectors $44_B$ and $44_C$. Other embodiments can use different sizes and/or different shapes for the connectors/connecting pins (e.g., one round, one square, etc.) to aid with the desired configuration of the connection between the e-cigarette 10 and the charger 46.

The window 54 can facilitate viewing, by a user, a display or a light on the e-cigarette 10 that is located to correspond with the window 54 when the e-cigarette 10 is connected with the charger 46. The window 54 can also be located to facilitate viewing a logo or other marking on the e-cigarette 10 when the e-cigarette 10 is connected with the charger 46. One or more windows 54 can be included on the charger 46 and located at any suitable location. FIG. 3A shows an exemplary embodiment of the charger 46 with two windows 54.

As shown in FIG. 3A, the charger 46 can be configured to electrically connect with the e-cigarette 10 to charge the battery 22 or to connect the e-cigarette 10 to, for example, a PC/computing device or some other processor using the charger 46 as a bridge. When acting as the bridge between the PC/mobile computing device and the e-cigarette 10, the charger 46 can translate the information or data going between the PC/computing device and the e-cigarette 10 to facilitate the exchange. In the bridging scenario, the charger 46 does not edit or change the data. The PC/mobile computing device are exemplary embodiments of processors that can be connected to the charger 46. Other embodiments can include, for example, a mobile phone (e.g., a "smart" phone), laptop or tablet computer or other similar device.

As shown in FIG. 3B, the charger 46 can include, for example, three connecting pins $48_{A-C}$, a charger control electronics 50, a charger memory 52. A window 54 (not marked in FIG. 3B) is shown in FIGS. 3A and 3C. The charger control electronics 50 can be electrically connected to a wire (not shown). The wire can also be connected to a connector (not shown). The connector can be any suitable connector including, for example, a universal serial bus (USB) connector.

The charger control electronics 50 can include a charger memory 52 and a charger processor (not shown). The charger 46 can be a synchronous state machine. The charger 46 can include one or more circuits in, for example, the charger control electronics 50. The one or more circuits can be digital circuits that allow the charger processor of the charger 46 to be in various states or modes. The states or modes of the charger processor can include, for example, idle, communication, charging, disconnect, or other modes. Any of the states or modes can include one or more sub-modes. For example, the communication mode can include a diagnostic sub-mode and an update sub-mode. The charger modes are described in greater detail below.

The charger control electronics 50 can collect data from the e-cigarette 10 and the charger memory 52 can store the collected data. For example, the charger control electronics 50 can collect data about the last several batteries and/or atomizer/fluid reservoirs 16 that were connected to the charger 46 and the number of hours the e-cigarette 10 has been in use.

The charger 46 can utilize software, hardware, firmware, and/or logic to perform a number of functions described herein. The charger 46 can include a combination of hardware and instructions to share information. The hardware, for example can include the control electronics 50 and/or the charger memory 52 (e.g., non-transitory computer-readable medium (CRM) database, etc.). The charger memory 52, as used herein, can include a number of processors capable of executing instructions stored by the memory resource. The charger memory 52 can be integrated in a single device or distributed across multiple devices. The instructions (e.g., computer-readable instructions) can include instructions stored on the charger memory 52 and executable by the charger processor and/or the charger memory 52 for providing control over the charger 46 and/or performing various steps discussed in relation to FIGS. 4 and 5, in an example.

In some embodiments, the charger 46 can include a wireless transmitter/receiver (not shown) to facilitate communication between the charger 46/e-cigarette 10 and a PC/mobile computing device. This can include the use of Bluetooth technology or other wireless protocols.

The e-cigarette 10 can be a synchronous state machine. The e-cigarette 10 can include one or more circuits in, for example, the control electronics 24. The one or more circuits can be digital circuits that allow the e-cigarette 10 to be in various states or modes. The states or modes of the e-cigarette 10 can include, for example, operation, charging, lower power sleep, light sleep, idle, disconnected, communication or other modes. Any of the states or modes can include one or more sub-modes. For example, the communication mode can include a diagnostic sub-mode and an update sub-mode.

An e-cigarette and a charger can be synchronous state machines. The e-cigarette and charger can each include one or more circuits. The one or more circuits can be digital circuits that allow the e-cigarette and the charger to be in various states or modes. The e-cigarette can synchronize with other devices (e.g., the charger, a case, etc.) and the charger can synchronize with other devices (e.g., the e-cigarette).

Figure 4:
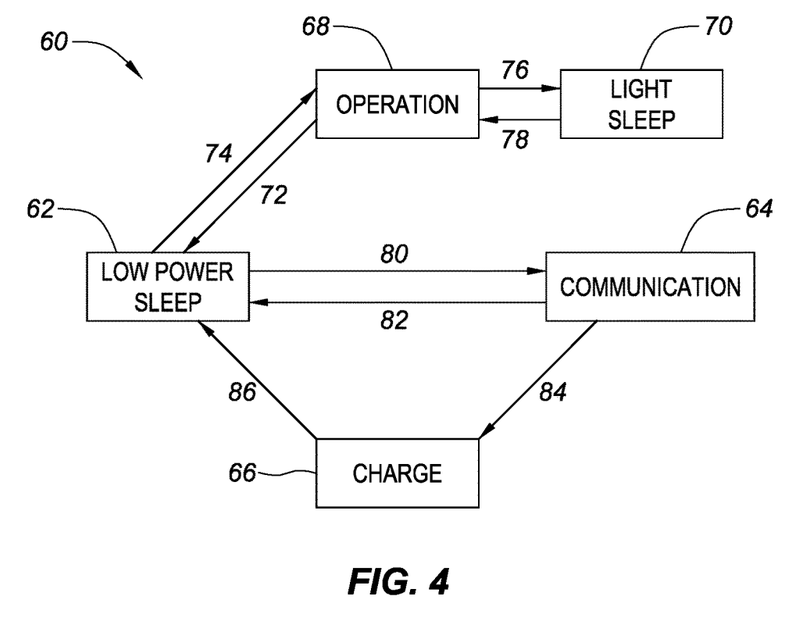
FIG. 4 is a state diagram that shows exemplary modes for an e-cigarette, consistent with various aspects of the present disclosure.

FIG. 4 is a state diagram that shows exemplary modes for an e-cigarette, consistent with various aspects of the present disclosure. The modes 60 of the e-cigarette 10 can include a low power sleep mode 62, a communication mode 64, a charge mode 66, an operation mode 68, and a light sleep mode 70. In some embodiments, the low power sleep mode 62 can be the default mode for the e-cigarette 10 in order to maximize battery life.

The low power sleep mode 62 can maximize an operating time of the battery 22 in the e-cigarette 10 by, for example, limiting power used during various processes. For example, the airflow sensor 26 can be turned off to conserve power. While in the low power sleep mode 62, the e-cigarette 10 cannot be used by a user (e.g., no puffs are possible). In some embodiments, the e-cigarette 10 can be in low power sleep mode 62 as a default mode and various actions and/or events can trigger a change in mode from the low power sleep mode 62 to a different mode.

For example, the low power sleep mode 62 can start when the atomizer/liquid reservoir 16 is disconnected from the e-cigarette 10 which is represented by connector link 72 in FIG. 4. As shown in FIG. 4, changes between some modes 60 (e.g., from the operation mode 68 to the communication mode 64, or from the charge mode 66 the communication mode 64, etc.) can require the e-cigarette 10 to transition through the low power sleep mode 62. Other configurations are possible for the arrangement of modes 60 in the synchronous machine arrangement. For example, in other embodiments, the communication mode 64 can be the transitional mode (instead of the lower power sleep mode 62 shown as in FIG. 2).

The e-cigarette 10 can be operated by a user in an operation mode 68. The operation mode 68 can be activated when a user uses the e-cigarette 10 (e.g., sucks/puffs on the e-cigarette 10). The operation mode 68 can also be trigged by, for example, connecting the atomizer/liquid reservoir 16 to the e-cigarette 10 (represented by connector link 74) as a user may intend to use the e-cigarette 10 after the connection (e.g., puff right after inserting a cartridge or connecting the atomizer/liquid reservoir 16).

The operation mode 68 can cause the e-cigarette 10 to, for example, activate the airflow sensor 26 during a puff causing the heating coil 30 to heat. In some embodiments, when the atomizer/liquid reservoir portion 16 is connected the e-cigarette 10 can switch from the low power sleep mode 62 to the operation mode 68. In other embodiments, when the atomizer/liquid reservoir 26, for example, is disconnected from the e-cigarette 10, the e-cigarette 10 can switch into the low power sleep mode 62.

During the operation mode 68, the e-cigarette 10 can periodically check for use (e.g., detect puffs by a user). As the frequency of use decreases, the frequency of checks for use can also decrease. For example, while in the operation mode 68, the e-cigarette 10 can check for use every 50 ms, and after 4 minutes of no use (e.g., no puffs by user) the e-cigarette 10 can increase the time between checks to four minutes.

The operation mode 68 can also have various sub-modes. For example, a stealth mode could vary one or more features of the e-cigarette 10 to minimize the visibility or other characteristic/feature of the e-cigarette 10. For example, the stealth mode could reduce or disable light from an LED 18, reduce power output so the heater coil 30 is a lower temperature which can cause the e-cigarette 10 to generate less vapour during use.

In some embodiments, the e-cigarette 10 can transition from the operation mode 68 to the light sleep mode 70 which can be represented by connector link 76 in FIG. 4. Similar to the low power sleep mode 62, the light sleep mode 70 can also reduce power usage of the e-cigarette to maximize battery life. In the light sleep mode 70 the airflow sensor 26 is still active but the e-cigarette 10 is in a reduced polling mode where the control electronics 24 check for usage less frequently compared to the operation mode 68. This allows the e-cigarette 10 to transition from the light sleep mode 70 to the operation mode 68 (represented by a connector line 76) in a shorter amount of time compared to transitioning from the low power sleep mode 62 to the operation mode 68.

In some embodiments, the power usage of the e-cigarette 10 while in the light sleep mode 70 can be equal to the power consumption of the e-cigarette 10 while in the low power sleep mode 62. In other embodiments, one of the modes could use less power (e.g., the low power sleep mode 62 could use less power than the light sleep mode 70 or the low power sleep mode 62 could use more power than the light sleep mode 70).

The low power sleep mode 62 can have various different sub-modes. For example, the e-cigarette 10 can be in a full sleep mode, a travel sleep mode, or a deep sleep mode. The full sleep mode can occur when the e-cigarette 10 is, for example, connected to a charger that is connected to a power supply and the battery is fully charged. The travel sleep mode can be, for example, while the e-cigarette 10 is connected to a charger that is not connected to a power supply. The deep sleep mode can occur, for example, when the e-cigarette 10 does not have the atomizer/liquid reservoir 16 connected (e.g., no puffs are possible) and the e-cigarette 10 is not connected to a charger. All sleep modes effectively reduce the power consumption (e.g., to a lowest possible level).

In some embodiments, the e-cigarette 10 can include a communication mode 64 as seen in FIG. 4. The communication mode 64 can be triggered by, for example, connecting the e-cigarette 10 to a charger 46 (represented by connector link 80). While in the communication mode 64, the e-cigarette 10 can detect the charger 46 and announce itself by sending a first signal or message to the charger 46 (e.g., passively or actively). In response, the charger 46 can send a second signal to the e-cigarette 10, acknowledging the announcement. The second signal can trigger the start of the communication mode 64. The communication mode 64 can end when the e-cigarette 10 receives, for example, a sleep message from the control electronics 24 or when the e-cigarette 10 switches to the charge mode 66. The communication mode 64 can end and the e-cigarette 10 can transition to the low power sleep mode 62 (represented by connector link 82) or the e-cigarette 10 can transition to the charge mode 66 (represented by connector link 84).

The sleep message can be generated by, for example, disconnecting the e-cigarette 10 from the charger 46. In another embodiment, if the e-cigarette 10 is connected to a charger 46 that is not connected to an external power source (e.g., external battery, charger, electronic device, connected to an AC outlet among others) the e-cigarette 10 can return and/or stay in the low power sleep mode 62 or the light sleep mode 70. The sleep message can cause the e-cigarette 10 to change from the charger mode 66 to the low power sleep mode 62 after the battery 22 is at a maximum charge. If the e-cigarette 10 is in the communication mode 64 and connected to the charger 46, the charger can also be in the communication mode 64.

When the e-cigarette 10 is in the communication mode 64 and connected to the charger 46, a charge message can cause the e-cigarette 10 switch from the communication mode 64 to the charge mode 66 and begin charging the battery 22. The e-cigarette 10 can continue charging the battery 22 until, for example, the charger 46 is disconnected or the e-cigarette 10 attains a full charge on a battery 22. If the charger 46 is disconnected from the e-cigarette 10 or the battery 22 has a full charge the e-cigarette 10 can switch from the charge mode 66 to the low power sleep mode 62.

As discussed above, in some embodiments, the e-cigarette 10 can be disposable. For disposable e-cigarettes the battery may not be rechargeable. In some embodiments, the disposable e-cigarette may not have low power modes. In this embodiment, the low power sleep and light sleep modes may not exist but other modes discussed herein may still be used and other additional modes may be included.

In some embodiments, the e-cigarette 10 can periodically change from a low power mode (e.g., the low power sleep mode 62 or the light sleep mode 70) to another mode. This periodic change can be thought of as "waking" from the low power mode to, for example, perform a task and/or monitor an operation, system or hardware. The periodic waking can control the various sleep modes (e.g., full sleep, travel sleep, and deep sleep) and can ensure the control electronics 24 is operating properly. For example, the e-cigarette 10 can wake to run a diagnostic operation in the diagnostic sub-mode of the communication mode 64. The periodicity of the waking can be controlled by a timer or triggered by some other event (e.g., connecting the e-cigarette 10 to the charger 46, the atomizer/liquid reservoir 16, a carry case, etc.). Connecting or disconnecting the e-cigarette 10 from an accessory or other device (e.g., a PC/computing device, a mobile phone, or other processor) can change the periodicity of the waking.

The communication mode 64 can include various other sub-modes. For example, after the e-cigarette 10 is in the communication mode 64, a diagnostic mode or an update mode can be started. The diagnostic mode can be used to diagnose various parts of the e-cigarette 10. For example, one more tests can be run on the constituent systems of the e-cigarette 10 (e.g., the control electronics 24, the battery 22, the atomizer/liquid reservoir portion 16, etc.). The diagnostic mode can also allow an e-cigarette memory to be collected (e.g., downloaded to a PC/mobile computing device, uploaded to a web site, etc.). Information stored in the e-cigarette memory can include, for example, the serial number of the e-cigarette 10, the serial number of the atomizer/liquid reservoir portion 16, or other information. The update mode can be used to, for example, provide firmware and/or software updates to the e-cigarette 10.

If the e-cigarette 10 is in the communication mode 64, the charger 46 can also synchronize to be in the communication mode 64 (shown in FIG. 3). Similarly, if the e-cigarette 10 is in the charge mode 66, the charger 46 can also synchronize to be a charge mode (discussed in more detail below). Other combinations of modes are possible when the e-cigarette 10 and the charger 46 synchronize (e.g., if the e-cigarette is in the lower power sleep mode 62, and connected to the charger 46, the charger 46 can be in an idle mode (discussed in more detail below)).

In some embodiments, the charger 46 can include the control electronics 50 that includes, for example, a memory 52. The charger memory 52 can collect data from the e-cigarette 10. For example, the charger memory 52 can collect data about the last several batteries that were connected to the charger 46 and the number of hours the e-cigarette 10 has been in use.

Figure 5:
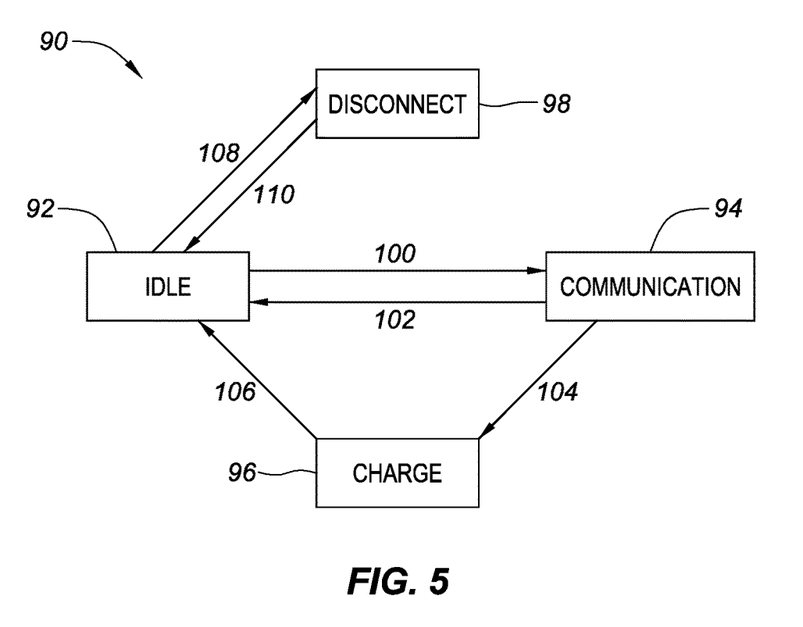
FIG. 5 is a state diagram that shows exemplary modes for the charger for the e-cigarette of FIG. 2, consistent with various aspects of the present disclosure.

FIG. 5 is a state diagram that shows exemplary modes for the charger for the e-cigarette of FIG. 2, consistent with various aspects of the present disclosure. The charger 46 can have various modes 90, including an idle mode 92, a communication mode 94, a charge mode 96, and a disconnect mode 98. The communication mode 94 and the charge mode 96 are described herein. The idle mode 92 can reduce energy used by the battery 22 by, for example, turning down a processor clock in the control electronics 24 and turning off peripheral electronics (e.g., the LED 18) and any other processes not necessary.

The charger 46 can be in an idle mode 92. In some embodiments, the idle mode 92 can be the default mode for the charger 46. If the charger 46 is not connected to the e-cigarette 10 or a PC/mobile computing device the charger 46 can be in the idle mode 92. If the e-cigarette 10 is initially connected to the charger 46 and then disconnected from the charger 46, the charger 46 can switch to the idle mode 92.

Connecting the e-cigarette 10 to the charger 46 can cause the charger 46 to switch from the idle mode 92 to the communication mode 94 (represented by connector link 100 in FIG. 5). Conversely, disconnecting the e-cigarette 10 from the charger 46 can cause the charger 46 to switch from the communication mode 94 to the idle mode 92 (represented by connector link 102 in FIG. 5).

In some embodiments, the charger 46 can determine or negotiate a rate of charging of the battery 22 in the e-cigarette 10. The negotiation can occur when the charger 46 and the e-cigarette 10 are connected and both in communication mode (e.g., the e-cigarette 10 in communication mode 64 and the charger 46 in communication mode 94). The charge message can be sent by the charger 46 to the e-cigarette 10. In response, the e-cigarette 10 can send a response signal back to the charger 46. The charger 46 can then determine a rate of charging for the battery 22.

The rate of charging can vary for a number of reasons. For example, connecting the e-cigarette 10 to a PC/mobile computing device via a USB connection (or other similar connection) may not allow the same charge rate compared to using a charger 46 with a charge block that accepts a charge block (e.g., as a USB plug) and also fits into electrical outlets (e.g., to metal prongs that fit into and electrical outlet) or other adapter connected to a typical household AC circuit (e.g., 120 v/60 Hz or 220V/50 Hz) or other external power source (e.g., external battery, etc.). As an example, the charger 46 can be rated for 150-500 mA. In some embodiments, a higher charge rate can be negotiated (e.g., 1000 mA) depending on the properties of the battery 22 and the type of connection supplying electricity to the charger 46.

The charger 46 can switch from the communication mode 94 to the charge mode 96 (represented by connector link 104 in FIG. 5) after the charge message/reply message are sent between the e-cigarette 10 and the charger 46 (e.g., the e-cigarette 10 is in control of a charge negotiation) and the charge negotiation is complete. In another embodiment, instead of the charge message being sent from the e-cigarette 10 to the charger 46, the charger 46 can send a message to the e-cigarette 10 after the e-cigarette 10 is connected to the charger 46 (e.g., the charger 46 is in control of the charge negotiation).

When the e-cigarette 10 has a battery 22 that is fully charged the e-cigarette can switch to a low power mode (e.g., the low power sleep mode 62, the light sleep mode 70, etc.) and the charger 46 can switch from the charge mode 96 to the idle mode 92 (represented by connector link 106 in FIG. 5). If the e-cigarette 10 in the charge mode 66 and is connected to the charger 46, the charger 46 can also synchronize to be in the charge mode 96.

The charger 46 can be placed in the disconnect mode 98 by, for example, disconnecting the charger 46 from the PC/computing device if the e-cigarette is already connected to the charger 46 (represented by connector link 108 in FIG. 5). The disconnect mode 98 can be ended by connecting the charger 46 to the PC/computing device (represented by connector link 110 in FIG. 5) if the charger is not connected to the PC/computing device.

Figure 6:
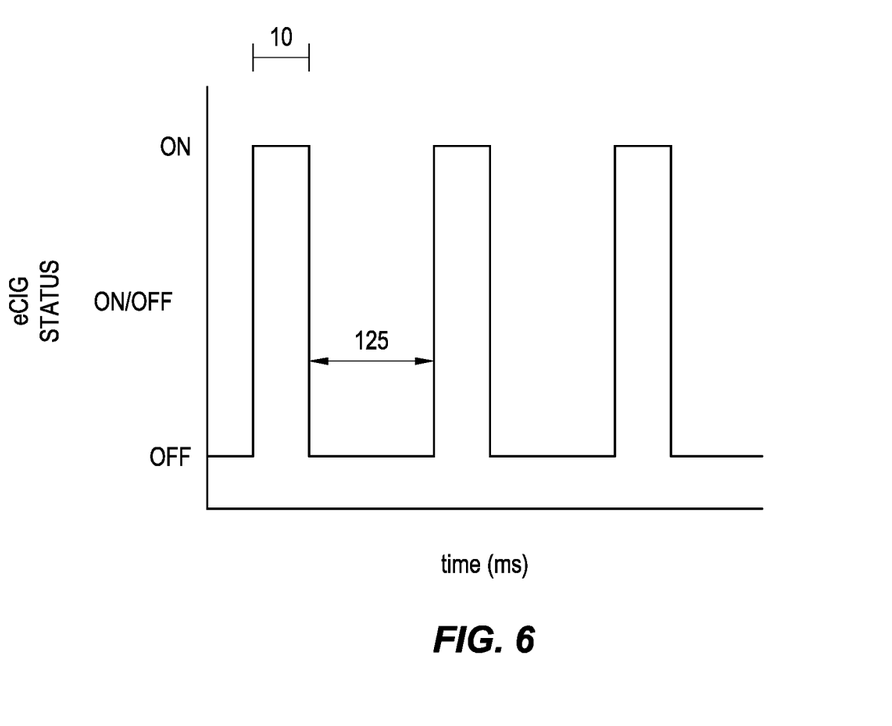
FIG. 6 is a chart that shows exemplary times that the e-cigarette can be turned on and turned off while in the light sleep mode, consistent with various aspects of the present disclosure.

FIG. 6 is a chart that shows exemplary times that the e-cigarette can be turned on and turned off while in the light sleep mode, consistent with various aspects of the present disclosure. The light sleep mode 70 can reduce energy used by the battery 22 by, for example, turning down a processor clock and turning off peripheral electronics and any other processes not necessary (e.g., the LED 18 etc.). In one example shown in FIG. 6, the e-cigarette 10 can be turned on for 10 ms and then turned off for 125 ms. In another embodiment, the e-cigarette 10 can be turned on for 50 ms and then turned off for 256 ms. Longer periods with the e-cigarette 10 off can be used in the low power modes (e.g., low power sleep mode 62, light sleep mode 70, etc.). The length of time the e-cigarette 10 is turned off can vary. For example, "on" times can range between 10-50 ms and "off" times can range between 125-4000 ms depending on the activity of the user with the e-cigarette 10. In one example, immediately after the e-cigarette 10 is used (e.g., the user sucks/puffs on the e-cigarette 10) a first off time can be 0 ms. After a first period of time the e-cigarette 10 can change to a second off time of 128 ms. After a second period of time the e-cigarette 10 can change to a third off time of 256 ms. The number of different off times can vary.

Figure 7:
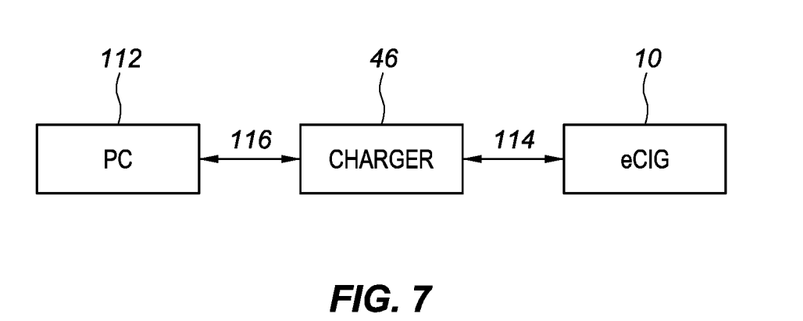
FIG. 7 is a block diagram illustrating data communication pathways between an exemplary e-cigarette and a processor, consistent with various aspects of the present disclosure.

FIG. 7 is a block diagram illustrating data communication pathways between an exemplary e-cigarette and a processor, consistent with various aspects of the present disclosure. FIG. 7 shows exemplary connections between an e-cigarette 10 and a charger 46 and the charger 46 and a processor 112 (e.g., a PC/computing device, a mobile phone, a remote server, etc.). A first connection 114 between the e-cigarette 10 and the charger 46 can be, for example, a serial connection. The serial connection is previously described above in more detail. A second connection 116 can be between the charger 46 and a processor 112 (e.g., a personal computer, a tablet computer, a mobile "smart" phone, or other similar device). The second connection 116 can be any suitable electrical connection between the charger 114 and the processor 116.

The e-cigarette 10 can connect to a charger 46 in order to charge the battery 22 (see FIG. 1) of the e-cigarette 10. In addition to this charging function, the charger 46 can exchange data with the e-cigarette 10. The data exchange can occur, for example, through a dedicated data line or signals obtained from a power line connecting the charger 46 and the e-cigarette 10 during charging. When a data line is used to transfer data between the e-cigarette 10 and the charger 46, the data line can be a physical wire connection or a wireless communication. In an embodiment, the data that can be transferred from the e-cigarette 10 to the charger 46 includes identifying data, such as a serial number, a calibration parameter, a batch code, a line number, or a barcode associated with the e-cigarette 10. In another embodiment, the data that can be transferred from the e-cigarette 10 to the charger 46 includes usage data, such as a number of puffs taken, an average length of puffs taken, a smoke juice level, a smoke juice flavor, or a location of use.

The charger 46 can act as a bridge connection between the e-cigarette 10 and the processor 112 (e.g., a personal computer (PC). While acting as the bridge connection between the e-cigarette 10 and the processor 112 the charger 46 does not add to or change the content of the data or information transmitted between the e-cigarette 10 and the processor 112. The processor 112 can be, for example, an external processor that is external to the e-cigarette 10 and to the charger 46. The external processor can be configured to communicate with the control electronics 24 and the charger control electronics 50 when the e-cigarette 10 is electrically connected to the charger 46.

The serial connection can be used to, for example, connect the e-cigarette 10 to the charger 46 to, for example, negotiate the charge rate of the e-cigarette 10 by the charger 46 or transmit signals or messages between the e-cigarette 10 and the charger 46 as described herein.

The second connection 116 can be used to, for example, update firmware on the e-cigarette 10 and/or the charger 46. The firmware can be transmitted from the memory that is part of the processor 112 or from a remote server, passing through the charger 46, to the e-cigarette 10. In other embodiments, the second connection 116 can permit the exchange of data (e.g., diagnostic data) between the processor 112 and the e-cigarette 10. In another embodiment, the second connection 116 can permit data stored on a memory device on the e-cigarette 10.

In summary, various embodiments of the present disclosure are directed to an electronic smoking device comprising a power supply portion comprising a power supply, an atomizer/liquid reservoir portion comprising a liquid reservoir, and an atomizer, the atomizer operable when connected to the power supply to atomize liquid stored in the liquid reservoir, and a control electronics, wherein the control electronics comprise a set of computer-readable instructions capable of executing an operation mode, a communication mode and a charge mode. The plurality of modes further comprise further comprise a low power sleep mode, and a light sleep mode. The control electronics comprise a plurality of connectors, wherein the plurality of connectors are inside the electronic smoking device and accessible through a corresponding plurality of apertures. The plurality of connectors further comprises three connectors that are configured to be electrically connected to a charger. The control electronics execute the communication mode is after the electronic smoking device is electrically coupled to a charger and the communication mode is configured to determine a charge parameter of the electronic smoking device. The charge parameter comprises at least one of a voltage and a current.

Some embodiments of an electronic cigarette charger include a first connection, wherein the first connection further comprises a plurality of connecting pins for electrically connecting to the electronic smoking device, a second connection, wherein the second connection is configured for electrically connecting to a computing device, a control electronics, wherein the control electronics comprises a memory, wherein the memory further comprises a set of computer-readable instructions capable of executing an idle mode, a communication mode and a charge mode. The plurality of modes further comprises a disconnect mode. The control electronics further comprise a plurality of connecting pins, wherein a portion of the plurality of connecting pins extend above a surface of the charger. The plurality of connecting pins further comprises three connecting pins that are configured to be electrically connected to the corresponding connectors on the electronic smoking device.

In various embodiments consistent with the present disclosure a system can include an electronic smoking device comprising a battery, an eCig memory storing a first set of computer-readable instructions, and control electronics configured to execute the first set of computer-readable instructions to place the electronic smoking device in a first plurality of modes; and a charger comprising a charger memory storing a second set of computer-readable instructions, and a charger processor configured to execute the second set of computer-readable instructions to place the charger in a second plurality of modes; wherein each of the first plurality of modes has at least one complementary mode in the second plurality of modes, and wherein the control electronics and the charger processor are configured to communicate and to negotiate a charge rate for charging the battery when the electronic smoking device is electrically connected to the charger. The first plurality of modes comprises an operation mode, a low power sleep mode, a light sleep mode, a communication mode, and a charge mode: and wherein the second plurality of modes comprises an idle mode, a disconnect mode, a communication mode, and a charge mode. The communication mode is initiated after the electronic smoking device is electrically connected to a charger, and wherein the communication mode is configured to determine a charge parameter of the electronic smoking device. The system can further comprise an external processor, wherein the external processor is external to the electronic smoking device and to the charger, and the external processor is configured to communicate with the control electronics when the electronic smoking device is electrically connected to the charger.

Aspects of the present disclosure are directed to a method of connecting an electronic smoking device to a charger, wherein the electronic smoking device is in a first mode and the charger is in a first charger mode, switching from the first mode of the electronic smoking device to a charging mode, switching from the first charger mode of the charger to a second charger mode, negotiating, by the electronic smoking device while in the second mode, a charge rate for charging a battery of the electronic smoking device by the charger while in the second mode, charging the battery at the negotiated charge rate. The first mode of the electronic smoking device is selected from the group consisting of a low power sleep mode, a communication mode, an operation mode, and a light sleep mode and wherein the second mode is a charging mode. The first charger mode of the charger is selected from a group consisting of an idle mode, a disconnect mode, and a communication mode, and wherein the second charger mode is a charging mode. The first mode further comprises a sub-mode, wherein the sub-mode is selected from the group consisting of a diagnostic mode, a stealth mode, an update mode, a full sleep mode, a travel sleep mode, and a deep sleep mode. The first charger mode further comprises a sub-mode, wherein the sub-mode is selected from the group consisting of a diagnostic mode and an update mode.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure. Moreover, it is noted that like reference numerals represent similar parts throughout the several views of the drawings.

The terms "including," "comprising" and variations thereof, as used in this disclosure, mean "including, but not limited to," unless expressly specified otherwise.

The terms "a," "an," and "the," as used in this disclosure, means "one or more," unless expressly specified otherwise.

Although process steps, method steps, algorithms, or the like, may be described in a sequential order, such processes, methods and algorithms may be configured to work in alternate orders. In other words, any sequence or order of steps that may be described does not necessarily indicate a requirement that the steps be performed in that order. The steps of the processes, methods or algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

Although several embodiments have been described above with a certain degree of particularity, those skilled in the art could make numerous alterations to the disclosed embodiments without departing from the spirit of the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various embodiments of the present disclosure are directed to an electronic cigarette battery housing apparatus including a power supply portion comprising a power supply, an atomizer/liquid reservoir portion comprising a liquid reservoir and an atomizer, the atomizer operable when connected to the power supply to atomize liquid stored in the liquid reservoir, and control electronics, wherein the control electronics are configured to execute a set of computer-readable instructions to place the electronic smoking device in an operation mode, a communication mode, and a charge mode. The control electronics are further configured to execute a set of computer-readable instructions to place the electronic smoking device in a low power sleep mode and a light sleep mode. The control electronics comprise a plurality of connectors, wherein the plurality of connectors are inside the electronic smoking device and accessible through a corresponding plurality of apertures. The plurality of connectors further comprises three connectors that are configured to be electrically connected to a charger. The control electronics executes the communication mode after the electronic smoking device is electrically coupled to a charger and the communication mode is configured to determine a charge parameter of the electronic smoking device. The charge parameter comprises at least one of a voltage and a current.

Some embodiments of an electronic cigarette charger include a first connection, wherein the first connection further comprises a plurality of connecting pins for electrically connecting to the electronic smoking device, a second connection, wherein the second connection is configured for electrically connecting to a computing device, charger control electronics, wherein the charger control electronics comprises a memory, wherein the memory further comprises a set of computer-readable instructions to place the charger in an idle mode, a communication mode and a charge mode. The charger control electronics are further configured to execute a set of computer-readable instructions to place the charger in a disconnect mode. The control electronics further comprises a plurality of connecting pins, wherein a portion of the plurality of connecting pins extend above a surface of the charger. The plurality of connecting pins further comprises three connecting pins that are configured to be electrically connected to the corresponding connectors on the electronic device.

In various embodiments consistent with the present disclosure a system can comprise a battery, an eCig memory storing a first set of computer-readable instructions, and control electronics configured to execute the first set of computer-readable instructions to place the electronic smoking device in a first plurality of modes; and a charger comprising a charger memory storing a second set of computer-readable instructions, and a charger processor configured to execute the second set of computer-readable instructions to place the charger in a second plurality of modes; wherein each of the first plurality of modes has at least one complementary mode in the second plurality of modes, and wherein the control electronics and the charger processor are configured to communicate and to negotiate a charge rate for charging the battery when the electronic smoking device is electrically connected to the charger.

Aspects of the present disclosure are directed to a method for charging an electronic smoking device comprising connecting the electronic smoking device to a charger, wherein control electronics of the electronic smoking device are in a first eCig mode and wherein a charger processor of the charger is in a first charger mode, switching the control electronics from the first eCig mode to a second eCig mode, switching the charger processor from the first charger mode to a second charger mode, negotiating, between the control electronics and the charger processor, while the electronic smoking device is in the second eCig mode, and while a charge rate for charging a battery of the electronic smoking device, the charger is in the second charger mode, and charging the battery at the negotiated charge rate. The first eCig mode of the electronic smoking device is selected from the group consisting of a low power sleep mode, a communication mode, an operation mode, and a light sleep mode, and wherein the second eCig mode is a charge mode. The first charger mode of the charger is selected from a group consisting of an idle mode, a disconnect mode, and a communication mode, and wherein the second charger mode is a charge mode. The first eCig mode comprises an eCig sub-mode selected from the group consisting of a diagnostic mode, a stealth mode, an update mode, a full sleep mode, a travel sleep mode, and a deep sleep mode. The first charger mode comprises a charger sub-mode selected from the group consisting of a diagnostic mode, and an update mode.

LIST OF REFERENCE SIGNS 10 electronic smoking device
12 end cap
14 power supply portion
16 atomizer/liquid reservoir portion
18 light emitting diode (LED)
20 air inlets
22 battery
24 control electronics
26 airflow sensor
28 atomizer
30 heating coil
32 wick
34 central passage
36 liquid reservoir
38 air inhalation port
40 controller circuitry
42 electrical contact apertures
44 electrical contacts (or connectors)
46 charger
48 connecting pins
50 charger control electronics
52 charger memory
54 window
56 wire
60 e-cigarette modes
62 low power sleep mode
64 communication mode
66 charge mode
68 operation mode
70 light sleep mode
72 connector link from operation mode to low power sleep mode
74 connector link from low power sleep mode to operation mode
76 connector link from operation mode to light sleep mode
78 connector link from light sleep mode to operation mode
80 connector link from low power sleep mode to communication mode
82 connector link from communication mode to low power sleep mode
84 connector link from communication mode to charge mode
86 connector link from charge mode to low power sleep mode
90 charger modes
92 idle mode
94 communication mode
96 charge mode
98 disconnect mode
100 connector link from idle mode to communication mode
102 connector link from communication mode to idle mode
104 connector link from communication mode to charge mode
106 connector link from charge mode to idle mode
108 connector link from idle mode to disconnect mode
110 connector link from disconnect mode to idle mode
112 processor
114 first connection
116 second connection

The invention claimed is:
1. An electronic smoking device comprising:
a power supply portion comprising a power supply,
an atomizer/liquid reservoir portion comprising a liquid reservoir and an atomizer, the atomizer operable when connected to the power supply to atomize liquid stored in the liquid reservoir, and
control electronics, wherein the control electronics are configured to execute a set of computer-readable instructions to place the electronic smoking device in an operation mode, a communication mode, a charge mode, light sleep mode, a low power sleep mode, a diagnostic mode, a stealth mode, an update mode, a full sleep mode, a travel sleep mode, and a deep sleep mode,
wherein the light sleep mode uses less power than the operation mode and the low power sleep mode uses less power than the light sleep mode, and the deep sleep mode uses less power than the light sleep mode.
2. The electronic smoking device of claim 1, wherein the control electronics comprise a plurality of connectors, wherein the plurality of connectors are inside the electronic smoking device and accessible through a corresponding plurality of apertures.

3. The electronic smoking device of claim 2, wherein the plurality of connectors further comprises three connectors that are configured to be electrically connected to a charger.

4. The electronic smoking device of claim 1, wherein the control electronics executes the communication mode after the electronic smoking device is electrically coupled to a charger and the communication mode is configured to determine a charge parameter of the electronic smoking device.

5. The electronic smoking device of claim 4, wherein the charge parameter comprises at least one of a voltage and a current.

6. The method of claim 1, wherein the control electronics check for usage of the electronic smoking device less frequently during the light sleep mode compared to the operation mode.

7. The method of claim 1, wherein the control electronics check for usage of the electronic smoking device less frequently during the low power sleep mode compared to the light sleep mode.

8. The method of claim 1, wherein the electronic smoking device, when in the light sleep mode or the low power sleep mode, can be turned off for times ranging between 125 to 4000 ms.

9. A charger for an electronic smoking device comprising:
a first connection, wherein the first connection further comprises a plurality of connecting pins for electrically connecting to the electronic smoking device,
a second connection, wherein the second connection is configured for electrically connecting to a computing device,
charger control electronics, wherein the charger control electronics comprises a memory, wherein the memory further comprises a set of computer-readable instructions to place the charger in an idle mode, a communication mode, a diagnostic mode, an update mode, and a charge mode.

10. The charger of claim 9, wherein the charger control electronics are further configured to execute a set of computer-readable instructions to place the charger in a disconnect mode.

11. The charger of claim 9, wherein the control electronics further comprise a plurality of connecting pins, wherein a portion of the plurality of connecting pins extend above a surface of the charger.

12. The charger of claim 11, wherein the plurality of connecting pins further comprises three connecting pins that are configured to be electrically connected to the corresponding connectors on the electronic smoking device.

13. A system comprising:
an electronic smoking device comprising
a battery,
an eCig memory storing a first set of computer-readable instructions, and
control electronics configured to execute the first set of computer-readable instructions to place the electronic smoking device in a first plurality of modes; and
a charger comprising
a charger memory storing a second set of computer-readable instructions, and
a charger processor configured to execute the second set of computer-readable instructions to place the charger in a second plurality of modes;
wherein the first plurality of modes comprises an operation mode, a low power sleep mode, a light sleep mode, a diagnostic mode, a stealth mode, an update mode, a full sleep mode, a travel sleep mode, and a deep sleep mode, where the light sleep mode uses less power than an operation mode and the low power sleep mode uses less power than the light sleep mode and the deep sleep mode uses less power than the light sleep mode, and
wherein each of the first plurality of modes has at least one complementary mode in the second plurality of modes, and wherein the control electronics and the charger processor are configured to communicate and to negotiate a charge rate for charging the battery when the electronic smoking device is electrically connected to the charger.

14. The system of claim 13, wherein the first plurality of modes further comprises a communication mode, and a charge mode, and wherein the second plurality of modes comprises an idle mode, a disconnect mode, a communication mode, and a charge mode.

15. The system of claim 14, wherein the communication mode is initiated after the electronic smoking device is electrically connected to a charger, and wherein the communication mode is configured to determine a charge parameter of the electronic smoking device.

16. The system of claim 13, further comprising an external processor, wherein the external processor is external to the electronic smoking device and to the charger, and the external processor is configured to communicate with the control electronics when the electronic smoking device is electrically connected to the charger.

17. A method for charging an electronic smoking device comprising:
connecting the electronic smoking device to a charger, wherein control electronics of the electronic smoking device are in a first eCig mode and wherein a charger processor of the charger is in a first charger mode,
switching the control electronics from the first eCig mode to a second eCig mode,
switching the charger processor from the first charger mode to a second charger mode,
negotiating, between the control electronics and the charger processor, while the electronic smoking device is in the second eCig mode, and while a charge rate for charging a battery of the electronic smoking device, the charger is in the second charger mode, and
charging the battery at the negotiated charge rate,
wherein the first eCig mode of the electronic smoking device is selected from the group consisting of a low power sleep mode, a communication mode, an operation mode, a light sleep mode, a diagnostic mode, a stealth mode, an update mode, a full sleep mode, a travel sleep mode, and a deep sleep mode, and wherein the second eCig mode is a charge mode.

18. The method of claim 17, wherein the first charger mode of the charger is selected from a group consisting of an idle mode, a disconnect mode, and a communication mode, and wherein the second charger mode is a charge mode.

19. The method of claim 17, wherein the first charger mode comprises a charger sub-mode selected from the group consisting of a diagnostic mode, and an update mode.

20. The method of claim 17, wherein the light sleep mode uses less power than an operation mode and the low power sleep mode uses less power than the light sleep mode.

* * * * *